United States Patent [19]

Tsukagoshi

[11] Patent Number: 4,936,312
[45] Date of Patent: Jun. 26, 1990

[54] BODY CAVITY INSERTING INSTRUMENT
[75] Inventor: Tsuyoshi Tsukagoshi, Fuchu, Japan
[73] Assignee: Olympus Optical Co., Ltd., Japan
[21] Appl. No.: 269,260
[22] Filed: Nov. 9, 1988
[30] Foreign Application Priority Data
Nov. 17, 1987 [JP] Japan ............................ 62-176255[U]
[51] Int. Cl.⁵ ............................................. A61B 10/00
[52] U.S. Cl. .................................... 128/749; 128/751; 128/756; 128/657
[58] Field of Search ............ 128/6, 642, 657, 749–753, 128/756–759; 604/95

[56] References Cited
U.S. PATENT DOCUMENTS

| | | | |
|---|---|---|---|
| 2,955,592 | 10/1960 | MacLean | 128/756 |
| 3,521,620 | 7/1970 | Cook | 128/772 |
| 3,613,664 | 10/1971 | Willson et al. | 128/756 |
| 3,799,151 | 3/1974 | Fukaumi et al. | 128/6 |

FOREIGN PATENT DOCUMENTS 53-98790 of 1978 Japan .

Primary Examiner—Randall L. Green
Assistant Examiner—Randy Shay
Attorney, Agent, or Firm—Ostrolenk, Faber, Gerb & Soffen

[57] ABSTRACT

A body cavity inserting instrument for use in an instrument for medical treatment comprises a flexible tubular member, a bending member made of an elastic material and an operating wire, said bending member having its front end fixed to the front end of said operating wire and its rear end fixed to the vicinity of the front end portion of said tubular member, thereby the front end portion of said tubular member being bent by allowing said bending member to bend by operating said operating wire on the proximal side of the instrument.

15 Claims, 3 Drawing Sheets

BODY CAVITY INSERTING INSTRUMENT

BACKGROUND OF THE INVENTION

The present invention relates to a body cavity inserting instrument, and more particularly, to a body cavity inserting instrument, such as an instrument for taking a cellular tissue in a cavity of a living body, which has a bending mechanism whose distal treatment portion is bendable to adjust its direction.

There is known a bending mechanism in an instrument for medical treatment of the kind as described above as shown in Japanese Utility Model Publication Sho 56 - 10329.

Specifically, this bending mechanism, as shown in FIG. 9, includes a loosely wound coil part 10a which is properly spaced between coil elements and which is disposed at the front end of a flexible tubular member 10 formed of closely wound coils and a member 11 for adjusting expansion and contraction of the loosely wound coil part which is made of a beltlike elastic plate and which is disposed within the coil part 10a in the longitudinal direction of the tubular member towards one side of the inner peripheral surface of the coil part 10a, the opposite ends of the member 11 being fixed to the inner peripheral surface of the coil part 10a. A fixing member 14 is fixed to the front end of the coil part 10a. The base of a brush 12 and the front end of an operating wire 13 are fixed to the fixing member 14. By pulling the operating wire 13 passing through the tubular member 10 to the proximal side of an instrument, a compressive force is applied to the tubular member 10 to reduce the space between coil elements of the coil part 10a on the side where the adjusting member 11 is not fixed. As a result, the coil part 10a bends drawing an arc on the side where the adjusting member 11 lies and thereby the brush 12 is bent to a direction shown by an arrow.

With a conventional bending mechanism as described above, however, only the opposite side of the coil part 10a where the adjusting member 11 is not fixed is reduced as described above and the side where the member 11 is fixed is kept stationary without expansion and contraction. Consequently, a bending angle is so small as to be insufficient in an operation of taking a tissue.

SUMMARY OF THE INVENTION

It is an object of the present invention to eliminate the disadvantages in a conventional instrument for medical treatment, such as an instrument for taking a tissue, by providing a body cavity inserting instrument which is capable of bending the distal end of the instrument in an increased angle to adjust its direction.

To this end, a body cavity instrument according to the present invention comprises a flexible tubular member whose front end portion is bendable, a bending member made of a beltlike elastic sheet whose rear end is fixed to the tubular member, and an operating wire movably inserted in the tubular member whose front end is fixed to the front end of the bending member so as to allow the bending member to be bowed to thereby bend the front end portion of the tubular member by operating the operating wire on the proximal end side of the instrument. With such arrangement, when the wire is pulled to the proximal end side, the bending member bends, so that a bending force acts on the front end portion of the tubular member to bend it. At this time, the bending tubular member is drawn out on its outer side and is contracted on the opposite side, so that the front end portion of the tubular member can be bent in a large angle.

According to the present invention, it is possible to make a bending angle of the distal end of an instrument for medical treatment, such as an instrument for taking a tissue large and a length of the bending portion small, thus eliminating the disadvantages in the prior art instrument.

DETAILED DESCRIPTION OF PREFERRED EMBODIMENTS

Figure 1A:
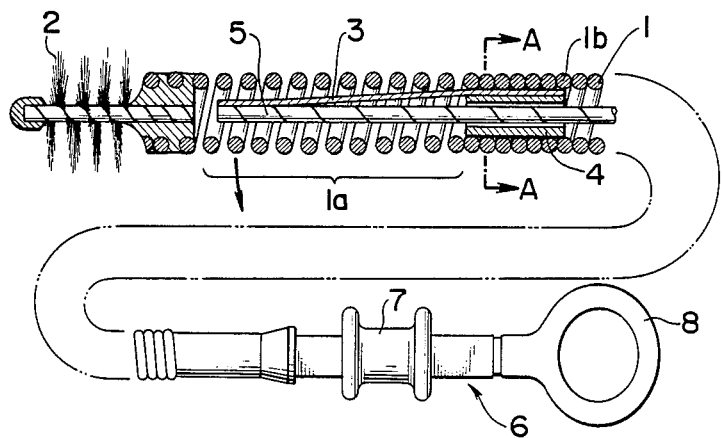
FIG. 1A is an enlarged sectional view of the distal end portion of an instrument for taking a tissue having a bending mechanism according to a first embodiment of the present invention and FIG. 1B is a sectional view taken along the line A—A of FIG. 1A.

In FIG. 1, which illustrates a first embodiment of the present invention, an instrument for taking a tissue has a bending mechanism comprising a flexible tubular member 1 formed of a coil tube, an operating wire 5 passing through the tubular member 1, whose rear end is fixed to a slider 7 which is movable relative to an operating body 6, and a bending member 3 made of a beltlike elastic sheet, which is disposed within the front end portion of the tubular member 1 and has its front end fixed to the front end of the operating wire 5 and its rear end fixed through a fixing member 4 to the inner surface of the tubular member 1.

Figure 1B:
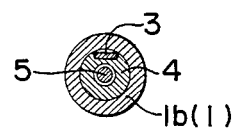

The tubular member 1 comprises a loosely wound coil part 1a which is located at the front end portion of the tubular member 1 in which the bending member 3 is disposed and which is formed by coil elements in properly spaced relationship with each other, and a closely wound coil part 1b connected to the loosely wound coil part 1a. The rear end of the bending member 3 is fixed through the short tubular fixing member 4 to the front end of the closely wound coil part 1b by a brazing operation or the like (FIG. 1B). In addition, the operating wire 5 is movably interposed within the closely wound coil part 1b by passing through the fixing member 4. A brush 2 for taking a tissue is fixed to the front end of the loosely wound coil part 1a by a brazing operation or the like. A small quantity of gap is provided between the front end of the loosely wound coil part 1a and the front free end of the bending member 3 which is disposed within the loosely wound coil part (FIG. 1A). This gap is provided for preventing the front end of the bending member 3 from interfering with the front end of the loosely wound coil part due to deformation of a bending part of the bending mechanism during the bending operation. In FIG. 1A, a ring 8, to receive a finger, is rotatably disposed at the rear end of the operating body 6.

Figure 2:
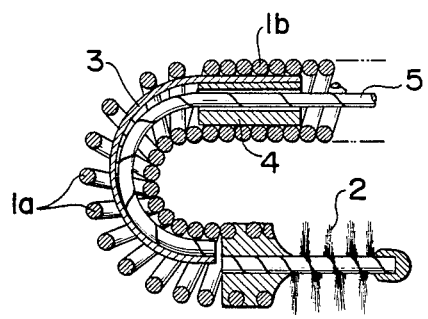
FIG. 2 is a sectional view illustrating a bending operation of the distal end portion of the instrument shown in FIG. 1A.

In operation, the operating wire 5 is allowed to move back by pulling the slider 7 out to the proximal side of the instrument with respect to the operating body 6. Then, the front end of the bending member 3 which end alone is fixed to the wire 5 is bent together with the front end of the wire 5 in a direction of an arrow shown in FIG. 1A. Consequently, the front end of the wire 5 applies a bending force to the inner surface of the front end of the loosely wound coil part 1a to bend the latter. By further pulling the wire 5 out to the proximal side of the instrument, as shown in FIG. 2, a space between coil elements on the side of the loosely wound coil part 1a to which the rear end of the bending member 3 is fixed is expanded and a space between coil elements on the side of the coil part 1a to which the bending member 3 is not fixed is reduced, so that the loosely wound coil part 1a can be bent up to approximately 180°. In addition, the front free end of the bending member 3 does not interfere with the front end of the loosely wound coil part 1a during the bending operation, enabling a sufficient angle of bending.

Consequently, since a bending angle of the brush 2 is largely increased, it is possible to take a tissue for cellular examination over a very wide range. In addition, the same bending angle can be obtained with length of the loosely wound coil part 1a (length of the bending part) more reduced than a conventional one. The feature of increasing a bending angle and reducing a length of the loosely wound coil part 1a (length of the bending part) are greatly effective in the case that the brush 2 is introduced into a bronchial periphery, for example, since they make possible a small turn.

Figure 3:
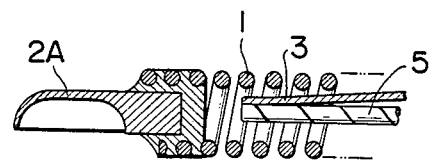
FIGS. 3 and 4 are sectional views illustrating other examples for the distal end portion of the treatment instrument shown in FIG. 1.
Figure 4:
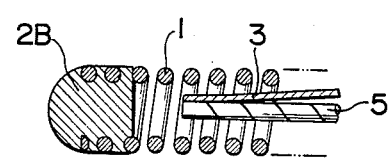

Although the above embodiment refers to an instrument provided with a brush for taking a tissue at the distal end portion thereof for taking a tissue, it is not limited to the brush. It is naturally possible that a cup 2A for biopsy forceps may be provided on the distal end portion of the instrument as shown in FIG. 3 or that the front end of the tubular member 1 may be formed in a globular shape to make a bendable guide member or the like.

The bendable guide member, which is used for an endoscope, is to guide the distal end of an endoscope by being inserted into a forceps channel thereof when the endoscope is inserted into a body cavity. Specifically, when an endoscope is inserted into a region where it is difficult to insert an endoscope, for example, the bile duct, after being inserted into the endoscope, the guide member is first inserted into the bile duct to guide the endoscope so as to make it possible to insert the endoscope into the bile duct.

Figure 5:
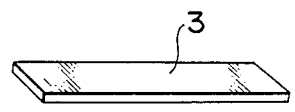
FIG. 5 is a perspective view illustrating a bending member in the bending mechanism shown in FIG. 1.
Figure 6:
FIG. 6 is a perspective view illustrating another example of the bending member.

Furthermore, while, in the bending mechanism according to the first embodiment of the present invention, the bending member 3 is formed in a beltlike flat strip of an elastic thin plate as shown in FIG. 5, it may be formed by twisting the bending member by about 90° at its center like a bending member 3A shown in FIG. 6.

With the bending member 3A formed as above, the distal end of the instrument does not bend in a two-dimensional manner but in a three-dimensional manner while twisting. This greatly improves the insertability of the distal end into branches of the bronchi or the like since such branches spread in three-dimensions.

Figure 7A:
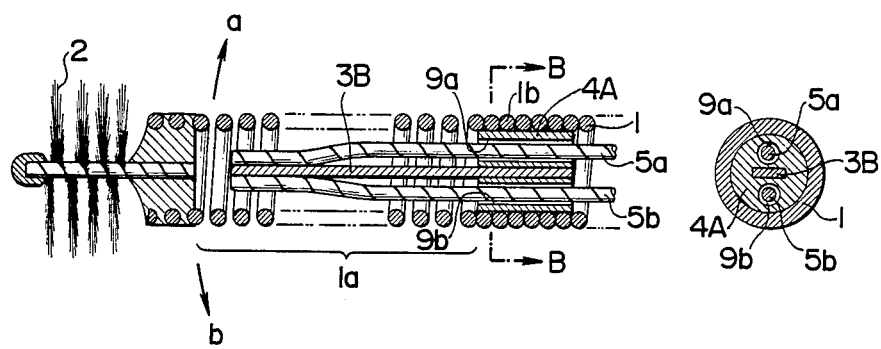
FIG. 7A is a sectional view illustrating a bending mechanism according to a second embodiment of the present invention and FIG. 7B is a sectional view taken along the line B—B of FIG. 7A.

In FIG. 7A, which illustrates a second embodiment of the present invention, an instrument for taking a tissue is constructed substantially in the same as that shown in FIG. 1 except members associated with a bending mechanism. Therefore, like reference characters designate corresponding parts in FIG. 1 and the description is omitted.

Figure 7B:
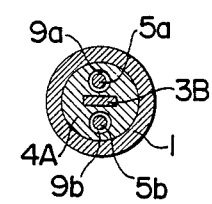

The instrument for taking a tissue according to the second embodiment has two wires 5a, 5b, each front end of which is fixed to the front end of a bending member 3B. The rear end of the bending member 3B is fixed to the center of a short column-shaped fixing member 4A (FIG. 7B) which is fixed to the front end of a closely wound coil part 1b of a tubular member 1 on the outer periphery of the fixing member 4A. Through-holes 9a, 9b are provided in the fixing member 4A in the axial direction of the latter, which holes are on opposite sides of the wide flat section of the bending member 3B so as to allow respective operating wires 5a, 5b to movably pass through. The proximal ends of the wires 5a, 5b are connected to respective sliders for operation (not shown).

With the instrument constructed as described above, the distal end of the instrument bends in a direction of an arrow a or b shown in FIG. 7 by pulling either of the operating wires 5a, 5b through its slider to the proximal end side. Thus, the distal end of the instrument can be optionally bent in two directions, so that it is possible to further obtain the effect of ease of insertability towards a tissue in a periphery or the like.

Figure 8A:
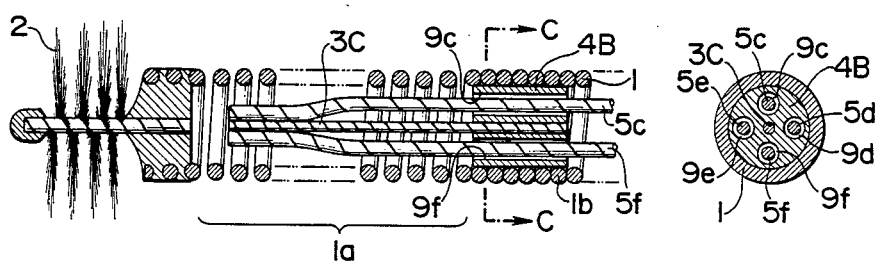
FIG. 8A is a sectional view illustrating a bending mechanism according to a third embodiment of the present invention and FIG. 8B is a sectional view taken along the line C—C of FIG. 8A.

In FIG. 8A, which illustrates an instrument for taking a tissue having a bending mechanism according to a third embodiment of the present invention, the instrument is also constructed in the same as that shown in FIG. 1 except members associated with the bending mechanism. Therefore, like reference characters designate corresponding parts and the description is omitted.

Figure 8B:
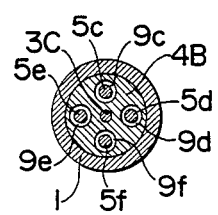
Figure 9:
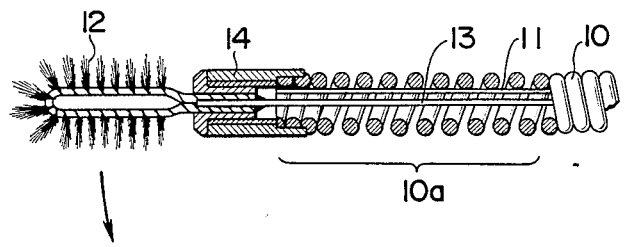
FIG. 9 is a sectional view illustrating an example of a conventional instrument for taking a tissue.

The bending mechanism of the third embodiment includes four operating wires 5c to 5f. A bending member 3C is made of a round bar-shaped elastic wire. Each front end of wires 5c to 5f is fixed to the front end of bending member 3C. The rear end of bending member 3C is fixed on the center of a short column-shaped fixing member 4B which is fixed to the front end of closely wound coil part 1b of the tubular member 1 (FIG. 8B). Four through-holes 9c to 9f are provided in the fixing member 4B in symmetry with the center thereof in the axial direction so as to allow four wires 5c to 5f to movably pass through respective through-holes. The proximal ends of operating wires 5c to 5f are connected to respective sliders (not shown) so as to operate wires 5c to 5f individually with sliders to move back and forth.

The arrangement of the instrument having the bending mechanism described above, makes it possible to bend in four directions. As a result, it is possible to obtain further effects of ease of introduction towards a tissue in the periphery.

While the bending mechanisms in the foregoing embodiments are applied to an instrument for taking a tissue, it will be noted that they can be applied to all instruments for medical treatment having a bending mechanism.

What is claimed is:

1. A body cavity inserting instrument comprising:

a flexible tubular member having a front end part that is bendable;

a bending member made of an elastic body and disposed within the front end part of said tubular member, said bending member having a rear end which is fixed to said tubular member;

said rear end of said bending member being the only portion of said bending member that is fixed to said tubular member; and at least one operating wire passing through said tubular member to move back and forth, said operating wire having a front end which is fixed to said bending member at its front end;

whereby the front end part of said tubular member is bent by allowing said bending member to bend by operating said operating wire on the proximal side of the instrument.

2. A body cavity inserting instrument according to claim 1 in which said tubular member is formed of a coil tue and the front end part of said tubular member in which said bending member is disposed in formed of a loosely wound coil which is provided with a space between coil elements.

3. A body cavity inserting instrument according to claim 1 in which said bending member has its rear end fixed to said tubular member through a short column-shaped fixing member disposed within said tubular member.

4. A body cavity inserting instrument according to claim 3 in which said fixing member has at least one through-hole for guiding said operating wire.

5. A body cavity inserting instrument according to claim 1 in which said bending member is belt-shaped and is formed of elastic sheet material.

6. A body cavity inserting instrument according to claim 5 in which said bending member is twisted transversely by about 90° at its longitudinally central region.

7. A body cavity inserting instrument according to claim 1 in which said bending member is formed of an elastic round wire rod having a rear end which is fixed to a short column-shaped fixing member at the transverse center of said fixing member, said column-shaped fixing member being fixed to a front portion of said tubular member.

8. A body cavity inserting instrument according to claim 1 further including a distal end portion operatively connected to said tubular member and extending forward thereof.

9. A body cavity inserting instrument according to claim 8 in which said distal end portion is provided with a treatment instrument for taking a tissue in a body cavity.

10. A body cavity inserting instrument according to claim 8 in which said distal end portion is a guide whose front end has a rounded surface.

11. A body cavity inserting instrument comprising:

a distal end portion provided with a member adapted for taking tissue;

a tubular member connecting said distal end portion to a proximal operating portion o the instrument and having a bending portion which is capable of bending in the vicinity of said connection of said distal end portion;

a bending member disposed within said bending portion and having its rear end fixed to said tubular member and its front end being a free end spaced from said distal end portion; and operating wire means movably passing through said tubular member and having its front end fixed to the front end of said bending member.

12. A body cavity inserting instrument according to claim 11 in which the space between said free end of said bending member and said distal end portion is sufficient for preventing interference between said bending member and said distal end portion when said bending portion is bent.

13. A body cavity inserting instrument according to claim 11 in which said operating wire means comprises two operating wires, which are disposed at opposite sides of the bending member.

14. A body cavity inserting instrument according to claim 13 in which the bending member is flat in shape, said operating wires being opposed in a depth direction of the bending member.

15. A body cavity inserting instrument having a proximal side and a distal side and comprising:

a flexible tubular member having a front end part that is bendable;

a bending member made of an elastic body and disposed within the front end part of said tubular member, said bending member having a rear end which is fixed to said tubular member; and at least one operating wire passing through said tubular member to move back and forth, said operating wire having a front end which is fixed to said bending member at its front end;

whereby the front end part of said tubular member is bent by allowing said bending member to bend by operating said operating wire on the proximal side of the instrument;

said bending member being belt-shaped and being formed of elastic material;

said bending member being twisted transversely by about 90° at its longitudinal central region.

* * * * *